United States Patent
Bar et al.

(10) Patent No.: US 8,492,619 B2
(45) Date of Patent: Jul. 23, 2013

(54) SEEDLESS PEPPER PLANT

(75) Inventors: Moshe Bar, Rishon Le-Zion (IL); Benjamin Nir, Maccabim-Reut (IL); Liora Lifschitz, Rehovot (IL)

(73) Assignees: Syngenta Participations AG, Basel (CH); Zeraim Gedera Ltd., Gedera (IL)

( * ) Notice: Subject to any disclaimer, the term of this patent is extended or adjusted under 35 U.S.C. 154(b) by 417 days.

(21) Appl. No.: 12/663,606

(22) PCT Filed: Jun. 13, 2008

(86) PCT No.: PCT/EP2008/057486
§ 371 (c)(1),
(2), (4) Date: May 17, 2010

(87) PCT Pub. No.: WO2008/152134
PCT Pub. Date: Dec. 18, 2008

(65) Prior Publication Data
US 2010/0227041 A1    Sep. 9, 2010

(30) Foreign Application Priority Data

Jun. 13, 2007 (IL) .......................................... 183902

(51) Int. Cl.
| | | |
|---|---|---|
| *A01H 5/00* | (2006.01) | |
| *A01H 5/08* | (2006.01) | |
| *A01H 5/10* | (2006.01) | |
| *A01H 1/02* | (2006.01) | |
| *A01H 1/04* | (2006.01) | |

(52) U.S. Cl.
USPC ...................... 800/317.1; 800/271

(58) Field of Classification Search
None
See application file for complete search history.

(56) References Cited

U.S. PATENT DOCUMENTS

| | | | | |
|---|---|---|---|---|
| 5,066,830 A | * | 11/1991 | Morrison et al. | 800/317.1 |
| 5,262,316 A | * | 11/1993 | Engler et al. | 800/294 |
| 2005/0055743 A1 | * | 3/2005 | Marie Edouard Nicolet et al. | 800/282 |

FOREIGN PATENT DOCUMENTS

| | | |
|---|---|---|
| WO | WO 97/40179 | 10/1997 |
| WO | WO 97/41240 | 11/1997 |
| WO | WO 98/28430 | 7/1998 |
| WO | WO 98/49888 | 11/1998 |
| WO | WO 2008/013450 | 1/2008 |

OTHER PUBLICATIONS

'Albayrak F1', from Anamas Seeds online catalog, accessed Feb. 2013.*
'Pazardjischki Kapia 794', PI 288945, deposited 1963.*
'Sofiiska Kapya', Grif 1549, deposited 1992.*
Charles et al., Journal of Horticultural Science, 1979, 54, 2, pp. 159-161.
Kato, J. Japan. Soc. hort. Sci., 58, 1, 1989, pp. 113-121.
Ishikawa et al., Hortscience, 39, 1, Feb. 2004, pp. 153-155.

* cited by examiner

*Primary Examiner* — David T Fox
(74) *Attorney, Agent, or Firm* — Karen Magri; Syngenta Participations AG

(57) ABSTRACT

The present invention generally relates to seedless pepper (SLP); and more specifically, it pertains to male sterile pepper plants having unique characteristics including the capability of growing edible seedless fruits, wherein the "seedless" trait is controlled by a genetic determinant independent of exogenous factors.

10 Claims, 2 Drawing Sheets

SEEDLESS PEPPER PLANT

CROSS-REFERENCE TO RELATED APPLICATIONS

This application is a national phase application of International Application No. PCT/EP2008/057486, filed Jun. 13, 2008, which claims priority to Israeli Application No. 183902, filed Jun. 13, 2007.

The present invention generally relates to seedless pepper (SLP); and more specifically, it pertains to male sterile seedless pepper having unique characteristics as set forth below.

Fruits are the result of the development of the ovary. In normal fruit development, the initiation of the fruit set depends on the successful completion of the pollination and fertilization process. Initiation of fruit development is generally repressed until fertilization occurs.

In general, the entire development of the fruit follows pollination and fertilization, and coincides with the maturation of the seeds. A fruit provides a suitable environment for the development of seeds.

External or internal factors may occasionally interfere with the normal process of fruit development, which then may become independent of pollination and fertilization such as, in parthenocarpic fruit setting. In parthenocarpic plants, fruit development and initiation is uncoupled from fertilization. The parthenocarpic characteristic can lead to the development of fruits with no or reduced seeds without pollination and fertilization. Parthenocarpy therefore refers to the development of the ovary into seedless fruit independent of the pollination and for fertilization process.

The parthenocarpic characteristic is well known in many plant species and may occur naturally or can be induced artificially with a variety of external stimuli such as, for example, application of different hormones. In most of the species the source of the parthenocarpic phenomenon, which results in the production of fruits with no or reduced seeds, may have a genetic and/or epigenetic basis. Parthenocarpy in plants may be seen as a mutation that reduces the plant's chances of survival and multiplication. One would logically assume that plants "want" to save their energy only for fruits that raise their chances of multiplication, and that, therefore, evolution would seek to eliminate plants producing seedless fruits or initiated fruits may drop in case no fertilization takes place. This is perhaps why the parthenocarpic phenomenon is so rare. In crop cultivation, it is used for essentially two purposes: A): to produce seedless fruits where seeds are viewed as undesirable (watermelon, cucumber) and B): to increase yield when fertilization conditions are adverse (tomato, eggplant).

Parthenocarpy is frequently accompanied by sterility, as in watermelon, but the characteristic is also found as an independent trait such as, for example, in cucumber and tomato.

Parthenocarpy can occur naturally or it can be artificially induced. Natural parthenocarpy may have a genetic basis and therefore be controlled by genetic determinants. The "seedless" trait can be obligatory or optional, that is it may be expressed all times or depending on the environmental conditions.

An artificially induced parthenocarpy may be the result of treatment of the plant and/or flower and/or ovary with exogenous agents such as dead pollen extract, or of applying growth regulating substances, either natural or synthetic. In fact, in protected cultivation such as, for example, in the greenhouse, exogenous applications of growth regulators are frequently used in order to induce the formation of seedless fruits with the aim of improving yield and fruit quality, but also in open field cultivation to prevent production losses under adverse conditions. However, these measures are cost and labor intensive and often also lead to only partial parthenocarpy. Furthermore, chemical treatment may also result in an increase of chemical residues on the fruits and in the soil and also malformations of the fruits are often to be observed.

Seedless sweet pepper cultivars based on natural parthenocarpy are not yet available; therefore, chemical manipulation was used to artificially induce parthenocarpy. Auxins, gibberellins and cytokinins (Sjut and Bangerth, 1982/83; Kim et al, 1992), as well as auxin transport inhibitors (Beyer and Quebe-deaux, 1974; Kim et al., 1992), have all been successfully applied to several fruit vegetable crops.

Fruit quality and yield are commonly dependent on the amount of seeds present in the fruit. High numbers of seeds usually lead to an increase in fruit size and quality. Pepper fruit yield and quality is particularly well known as being highly dependent on the amount of seeds. Moreover, pepper is usually very sensitive to setting. Once the plant starts this process it turns the majority of its energy to setting. As a result of this competition for limited energy and assimilate resources, subsequent set and growth of fruits is inhibited as well as growth of leaves, branches and roots. An increasing number of seeds reduce plant growth further.

This sensitivity of pepper plants to setting is one of the reasons for the "flushing" phenomenon, which leads to cyclic fluctuations of fruit set and thus in pepper fruit yield with weeks of high yield alternating with weeks of low yield. This irregular harvest pattern is an important problem for pepper growers because it makes it difficult for the growers to meet the market demand during growing seasons and further leads to fluctuations in labor demand in the greenhouses.

In other species, tomato for example, the sensitivity to setting is much lower. Tomatoes can produce relatively good yield and quality fruits even when they have few seeds, or continue to grow even when the fruits have a large amount of seeds. Artificial tools can ensure fruit setting in some species where fertility conditions are adverse. In tomato, spraying of a special hormone (auxin) can induce fruit setting, even without seeds.

Heuvelink and Körner (2001) tested the working hypothesis that growing parthenocarpic fruit on pepper plants may at least reduce the flushing problem in pepper growth and further yield high quality pepper fruits.

Heuvelink and Körner (2001) induced parthenocarpic fruit growth in pepper by preventing self—pollination and applying auxin to the stigma. They could confirm that parthenocarpic fruit growth resulted in a more regular fruit set and yield and thus has the potential to reduce the problem of flushing.

Induction of parthenocarpic growth by external application of plant hormones or other inducing agents is, however, labour and cost intensive and may raise environmental concerns due to increased amounts of chemical residues on or in the fruits or the soil. This approach is therefore not practical for commercial pepper production. There was therefore a need for genetic solutions that avoid cyclic fluctuations in pepper yield, but would instead guarantee a continuous supply with high quality pepper fruits.

The present invention now offers such a solution which is suitable for commercial use by providing a parthenocarpic pepper plant which grows seedless fruits, wherein setting of seedless fruits is independent of the pollination and fertilization process and/or of treatment with exogenous agents, but controlled by a genetic determinant that is stable and thus can be stably inherited to progeny plants and introgressed into commercial pepper varieties.

This invention also offers the advantage of improved options for insect and disease control. Viral diseases of pepper are generally transmitted by aphids. These insects can be controlled with the use of mechanical means such as tissue nets. These insect control measures have, however, the disadvantage that also beneficial insects are prevented from accessing the pepper plants and therefore no insect-mediated pollination can occur. The present invention now permits protecting pepper plants from aphid infestations and thus from aphid-transmitted virus infections without interfering with normal fruit setting and fruit harvest and without the need for chemical pesticides, thus reducing the costs of insect and disease control.

In particular, the present invention provides a pepper plant, which grows seedless fruits, wherein the "seedless" trait is controlled by a genetic determinant independent of the pollination and fertilization process and also independent of treatment with parthenocarpy-inducing plant hormones including auxins, gibberellins and cytokines, auxin transport inhibitors, or others and/or other parthenocarpy-inducing exogenous factors and/or exogenously administered parthenocarpy-inducing agents such as growth regulating substances, either natural or synthetic, or plant extracts such as, for example, dead pollen extract.

In one embodiment of the invention, a pepper plant is provided, which grows seedless fruits, wherein the "seedless" trait is controlled by a genetic determinant and independent of exogenous treatment with parthenocarpy-inducing plant hormones.

In one embodiment, said pepper plant according to the invention grows seedless fruits independent of treatment with plant hormones selected from the group consisting of auxins, gibberellins and cytokines, auxin transport inhibitors, and others.

In one embodiment of the invention, a pepper plant is provided, which grows seedless fruits, wherein the "seedless" trait is independent of the pollination and fertilization process.

In one embodiment, said pepper plant according to the invention grows seedless fruits, which are at least 95%, particularly at least 98%, particularly at least 99% seedless.

In one embodiment, said pepper plant according to the invention grows seedless fruits, which are 100% seedless.

In one embodiment, a plant according to the invention and as described herein before is provided, wherein at least 40%, particularly at least 50%, particularly at least 60%, particularly at least 70%, particularly at least 80%, particularly at least 90%, but especially 100% of the fruits grown on said plant are seedless.

In one embodiment, a plant according to the invention and as described herein before is provided, wherein at least 40%, particularly at least 50%, particularly at least 60%, particularly at least 70%, particularly at least 80%, particularly at least 90%, but especially 100% of the fruits grown on said plant are seedless fruits, which are at least 95%, particularly at least 98%, particularly at least 99% seedless.

In one embodiment, a plant according to the invention and as described herein before is provided, wherein at least 40% of the fruits grown on said plant are seedless fruits, which are at least 95%, particularly at least 98%, particularly at least 99% seedless.

In one embodiment, a plant according to the invention and as described herein before is provided, wherein at least 60% of the fruits grown on said plant are seedless fruits, which are at least 95%, particularly at least 98%, particularly at least 99% seedless.

In one embodiment, a plant according to the invention and as described herein before is provided, wherein at least 70% of the fruits grown on said plant are seedless fruits, which are at least 95%, particularly at least 98%, particularly at least 99% seedless.

In one embodiment, a plant according to the invention and as described herein before is provided, wherein at least 80% of the fruits grown on said plant are seedless fruits, which are at least 95%, particularly at least 98%, particularly at least 99% seedless.

In one embodiment, a plant according to the invention and as described herein before is provided, wherein at least 90% of the fruits grown on said plant are seedless fruits, which are at least 95%, particularly at least 98%, particularly at least 99% seedless.

In one embodiment, a plant according to the invention and as described herein before is provided, wherein at least 95% of the fruits grown on said plant are seedless fruits, which are at least 95%, particularly at least 98%, particularly at least 99% seedless.

In one embodiment, a plant according to the invention and as described herein before is provided, wherein at least 99% of the fruits grown on said plant are seedless fruits, which are at least 95%, particularly at least 98%, particularly at least 99% seedless.

In one embodiment, a plant according to the invention and as described herein before is provided, wherein 100% of the fruits grown on said plant are seedless fruits, which are at least 95%, particularly at least 98%, particularly at least 99% seedless.

In one embodiment, a plant according to the invention and as described herein before is provided, wherein 40% of the fruits grown on said plant are seedless fruits, which are 100% seedless.

In one embodiment, a plant according to the invention and as described herein before is provided, wherein 60% of the fruits grown on said plant are seedless fruits, which are 100% seedless.

In one embodiment, a plant according to the invention and as described herein before is provided, wherein 80% of the fruits grown on said plant are seedless fruits, which are 100% seedless.

In one embodiment, a plant according to the invention and as described herein before is provided, wherein 90% of the fruits grown on said plant are seedless fruits, which are 100% seedless.

In one embodiment, a plant according to the invention and as described herein before is provided, wherein 95% of the fruits grown on said plant are seedless fruits, which are 100% seedless.

In one embodiment, a plant according to the invention and as described herein before is provided, wherein 98% of the fruits grown on said plant are seedless fruits, which are 100% seedless.

In one embodiment, a plant according to the invention and as described herein before is provided, wherein 100% of the fruits grown on said plant are seedless fruits, which are 100% seedless.

In particular, the present invention provides a pepper plant according to the invention and as described herein, which grows seedless fruits which are edible and of high quality.

In one embodiment, the present invention provides a pepper plant growing seedless fruits which are edible and of high quality and suitable of being used as fresh produce, as fresh cut produce, or for processing such as, for example, canning.

In one embodiment, said pepper plant according to the invention is capable of setting seedless fruits throughout the plant. In particular, fruit setting starts at the first nodes of a branch and progresses along the length of the entire branch. In one embodiment, said plant grows particularly two fruits per node in about 20%, particularly in about 40%, particularly in about 60% of the nodes.

In one embodiment, said pepper plant according to the invention shows fruit setting at all seasons that is also under unfavourable conditions within the context of the climatic conditions of Israel or comparable climes.

In one embodiment, said pepper plant according to the invention grows normal looking fruits, which comply with commercial quality standards such as defined, for example, in the United States Standards for Grades of Peppers (USDA, Agricultural Marketing Service, Fruit and Vegetable Programs, Fresh Products Branch).

In still another aspect of the invention, the plant according to the invention and as described herein before carries fruit, which, at maturity, weigh over 2 grams or are longer than 1 cm and have a diameter of over 0.5 cm, when said plant is grown under growing conditions generally used by growers in regular cropping practice, in open field or in protected cultivation.

The pepper plant according to the invention and as described herein before may grow a sweet pepper including a dolce-type pepper, a bell pepper, a big rectangular pepper, a conical pepper, a long conical pepper or a blocky-type pepper. The fruit of said plant at maturity may be an evergreen, a yellow, orange, ivory, brown, purple, or red fruit.

The plant according to the invention may be a hot pepper plant, e.g. a mildly pungent pepper used for the fresh market and for processing including the long, heart-shaped, thin-fleshed Ancho-type and the long, blunt-ended, thin-fleshed Tuscan-type pepper, the slightly more pungent Chili pepper fruit with medium flesh thickness, and a pungent pepper used in both the fresh market and for processing including the long, cylindrical-thick fleshed Jalapeno, the small, slender, tapering Serrano and the irregularly shaped, thin-fleshed Cayenne pepper.

The plant according to the invention and as described herein before may be an inbred, a dihaploid or a hybrid and/or a male sterile.

In one embodiment, said pepper plant according to the invention and as described herein is male sterile.

In one embodiment, a pepper plant is provided, particularly a seedless pepper plant according to the invention and as described herein, which grows pepper fruits which are red pigmented in the mature and dark green pigmented in the premature (unripe) stage.

In one embodiment of the invention, said pepper fruits at maturity have very sweet taste with a Brix of between about 7° to about 14°, particularly of between about 7.5° to about 12°, particularly of between about 8° to about 11°.

In one embodiment of the invention, said pepper fruits have a conic-like shape, between bell and classic conic and a size of between about 2 to 4 cm by about 3 to 4 cm in diameter.

In one embodiment, a pepper plant is provided, particularly a seedless pepper plant according to the invention and as described herein, which grows a pepper fruit which is red pigmented in the mature and dark green pigmented in the premature (unripe) stage; have very sweet taste with a Brix of between about 7° to about 14°, particularly of between about 7.5° to about 12°, particularly of between about 8° to about 11°; have a conic-like shape, i.e., between bell and classic conic and a size of between about 2 to 4 cm by about 3 to 4 cm in diameter.

In one embodiment, the pepper plant according to the invention and as described herein before contains a "seedless" trait, which is obtainable from a hybrid pepper plant selected from the group of hybrids consisting of *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X. Seeds for growing such hybrid plants have been deposited with NCIMB, Aberdeen AB21 9YA, Scotland, UK on May 26, 2008 under accession number NCIMB 41558, NCIMB 41559, NCIMB 41560, NCIMB 41561 and NCIMB 41562, respectively.

In one embodiment of the invention, the "seedless" trait or a plant comprising said trait is obtainable from any of the hybrid lines grown from the deposited seeds by growing the F2 progeny of said hybrid. In particular, the "seedless" trait or a plant comprising said trait is obtainable from any of the deposited hybrid lines by i) germinating seed of said lines and growing a mature, fertile plant therefrom; ii) inducing self-pollination of said plant grown under (i), growing fruits and harvesting the fertile seeds therefrom, and iii) growing plants from the seeds harvested under ii) and selecting plants which grow seedless fruits.

In one embodiment, the invention relates to plant material obtainable from a plant according to the invention and as described herein before including, but without being limited thereto, leaves, stems, roots, flowers or flower parts, fruits, pollen, egg cells, zygotes, seeds, cuttings, cell or tissue cultures, or any other part or product of the plant which still exhibits the seedless phenotype according to the invention, particularly when grown into a plant.

The invention further relates to plant parts obtainable from a plant according to the invention and as described herein before including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the seedless phenotype according to the invention, particularly when grown into a plant.

The invention further relates to an agronomic method of producing seedless pepper fruits comprising the steps of
  i) providing a pepper plant according to the invention and as characterized herein before;
  ii) multiplicating/propagating said pepper plant
  iii) optionally preventing pollination of said pepper plant by using, e.g., male fertile pepper plants, functional male sterile pepper plants, or emasculation;
  iv) allowing the plant to grow seedless pepper fruits; and
  v) harvesting said pepper fruits.

In one embodiment of the invention, the multiplication or propagation of the pepper plant is done either through seeds or by vegetative propagation.

The invention further relates to a method of producing a seedless pepper plant comprising the steps of
  i) providing seeds of an F1 hybrid made by crossing of a seedless pepper plant as a female line and a male-fertile (seed-bearing) pepper plant as a male line;
  ii) germinating said seed and growing a mature, fertile plant therefrom;
  iii) inducing self-pollination of said plant grown under (ii), growing fruits and harvesting the fertile seeds therefrom, and
  iv) growing plants from the seeds harvested under iii) and selecting plants which grow seedless fruits.

In one embodiment, the hybrid seed used in said method according to the invention is the hybrid seed, which is obtainable from a hybrid pepper plant selected from the group of hybrids consisting of *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X, grown from seeds deposited with NCIMB, Aberdeen AB21 9YA, Scotland, UK on May 26, 2008 under accession number NCIMB 41558, NCIMB 41559, NCIMB 41560, NCIMB 41561 and NCIMB 41562, respectively.

DEFINITIONS

Figure 1:
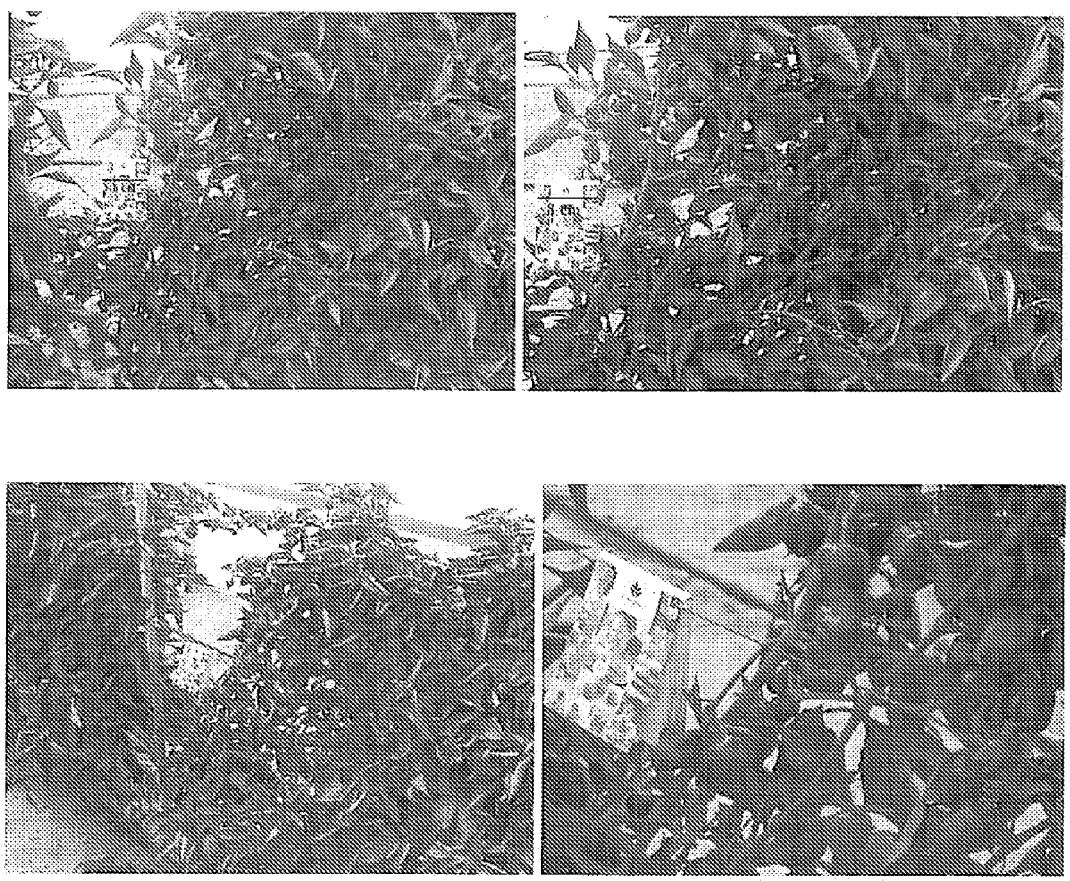
FIG. 1: SLP plant in the net house, Netiv Haasara village Israel. The "one bite" type variety "AR06-F3-255-1". This variety was used as SLP source in the deposited hybrids.
Figure 2:
FIG. 2: Fruits from Yellow blocky SLP variety "SD07-3-5", as resulting from the hybrid made between "AR06-F3-255-1" and a F2 plant of a yellow blocky pepper variety.
Figure 3:
FIG. 3: Fruits from Red conic SLP variety "SD07-2-77", as resulting from the hybrid made between "AR06-F3-255-1" and a F2 plant of a red Kapya type pepper variety.

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

"Parthenocarpy", as used herein, refers to the production of fruits without fertilization and it permits seedless fruits to be obtained. Parthenocarpy is favored by certain environmental conditions such as high or low daytime or nocturnal temperatures, a low level of light and high humidity. Parthenocarpy can occur naturally or it can be artificially induced. Natural parthenocarpy is produced by (epi)genetic causes and can be obligatory or optional, in other words, depending on the environmental conditions.

"Seedless pepper fruit", as used herein, refers to a pepper fruit obtained independently of the pollination and/or fertilization process, and/or independent of treatment with parthenocarpy-inducing plant hormones and/or other parthenocarpy-inducing exogenous factors and/or exogenously administered parthenocarpy-inducing agents.

A seedless pepper fruit which is "XX %" seedless, refers to a fruit wherein only "100–XX %" of the ovaries present in said fruit develop into seeds. For example, a seedless pepper fruit which is "95%" seedless, refers to a fruit wherein only "100–95%" of the ovaries present in said fruit, that is 5% of the ovaries, develop into seeds.

A "seedless pepper plant" as used herein, refers to a pepper plant growing a seedless pepper fruit as defined herein, including a pepper plant wherein only "100–XX %" of the fruits present on said pepper plant are seedless, particularly 95% and up to 100% seedless.

As used herein, "edible fruit" and "fresh edible fruit" refer to fruit picked from the plant that are suitable for human consumption.

As used herein, "exogenous factors or agents" refer to factors or agents that upon exogenous application to the plant, particularly to the reproductive parts of the plant such as, for example, the stigma, are capable of inducing an artificial parthenocarpy in the treated plant. Such "exogenous factors or agents" may be, for example, dead pollen extract, growth regulating substances, either natural or synthetic such as plant hormones including auxins, gibberellins and cytokines, auxin transport inhibitors, or others.

As used herein, the term "trait" refers to characteristic or phenotype, e.g., mature fruit color or a disease resistance such as TSWV resistance. A trait may be inherited in a dominant or recessive manner, or in a partial or incomplete-dominant manner. A trait may be monogenic (i.e. determined by a single locus) or polygenic (i.e. determined by more than one locus) or may also result from the mutual interaction among genes or interaction of one or more genes with the environment. A dominant trait results in a complete phenotypic manifestation at heterozygous or homozygous state; a recessive trait manifests itself only when present at homozygous state.

The term "pericarp" as is known in the art refers to the wail of a matured ovary. Specifically, pepper fruit pericarp refers to the fruit wall, which is the colored, edible part of the pepper fruit. As used herein, the term "thick pericarp" refers to a pericarp width of at least 5 mm, preferably at least 8 mm. As used herein the term "selfing" refers to a controlled self-pollination of a plant, i.e. contacting pollen and ovule produced by the same plant. The term "crossing" refers to controlled cross-pollination, i.e. contacting pollen and ovule each produced by a different plant.

The term "plant vigor" is used herein in its broadest sense, referring to the plant general strength.

As used herein, a "fruit crop" refers to the crop of a single plant, or preferably, to the fruit crop obtained from pepper plants grown on a commercial scale.

The term "commercial pepper line or variety" as is used herein refers to a pepper plant which is available commercially such as, for example, pepper variety having sweet, edible fruit with a thick pericarp. Typically, the commercial pepper variety may have fruit with a blocky, Californian-type fruit shape. Examples of commercial pepper varieties include, without however being limited to, for example sweet pepper commercial cultivars of the "bell" type such as Cannon (Zeraim Gedera); Vergasa (Syngenta Seeds); Bardenas (Syngenta Seeds), Roxy (Syngenta Seeds), Yolo Wonder (Syngenta Seeds), etc.

"Low temperature" with regard to pepper plant growth according to the present invention refers to temperature in the range of 10°-12° C. and below depending on the variety used.

As used herein, the term "allele(s)" means any of one or more alternative forms or variant forms of various genetic units identical or associated with different forms of a gene or of any kind of identifiable genetic element, all of which alleles relate to at least one trait or characteristic. In a diploid cell, the two alleles of a given gene occupy corresponding loci on a pair of homologous chromosomes and are, therefore, alternative in inheritance.

Such alternative or variant forms may be the result of single nucleotide polymorphisms, insertions, inversions, translocations or deletions, or the consequence of gene regulation caused by, for example, by chemical or structural modification, transcription regulation or post-translational modification/regulation.

In some instances it may be more accurate to refer to "haplotype" (i.e. a haplotype is a combination of alleles at several or multiple linked loci (on the same chromosome) that are transmitted together) instead of "allele", however, in those instances, the term "allele" should be understood to comprise the term "haplotype". Alleles are considered identical when they express a similar phenotype, but in some cases it can happen that different alleles also express a similar phenotype.

Differences in sequence are possible but of less importance as long as they do not influence phenotype.

An allele associated with a quantitative trait may comprise alternative or variant forms of various genetic units including those that are identical or associated with a single gene or multiple genes or their products or even a gene disrupting or controlled by a genetic factor contributing to the phenotype represented by said QTL.

A "genetic determinant" is defined herein as a nucleotide sequence, preferably a DNA sequence that may comprise sequences with various genomic functions such as genes and regulatory elements regions. Genetic determinant may also refer to a nucleotide construct and may be comprised in a vector. Alternatively, a genetic determinant may be transferred from one plant to another by chromosomal recombination after crossing said plants. A genetic determinant may in principle comprise genetic material originating from one or more species.

In particular, genetic determinant as used herein refers to a single gene or multiple genes, a QTL or a haplotype, that determines expression of the seedless phenotype in a pepper plant.

A "gene" is defined herein as a hereditary unit consisting of a sequence of DNA that occupies a specific location on a chromosome and that contains the genetic instruction for a particular characteristics or trait in an organism.

A "locus" is defined herein as the position on a genetic map that a given gene or any other genetic element or factor contributing to a trait occupies on a chromosome of a given species.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

The terms "chromosome" is meant to include, and thus used herein synonymously with, the terms "linkage group" and/or "chromosome equivalent of linkage group", respectively As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

Homozygosity is defined as absence of segregation after selfing of an individual plant or, if crossed, absence of segregation in F1.

As used herein, the terms "hybrid", "hybrid plant," and "hybrid progeny" refers to an individual produced from genetically different or unlike parents (e.g., a genetically heterozygous or mostly heterozygous individual) (Rieger et al., 1968).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to a stable inbred line issued from anther culture. Some pollen grains (haploid) cultivated on specific medium and circumstances can develop plantlets containing n chromosomes. These plantlets are than "doubled" and contain 2n chromosomes. The progeny of these plantlets are named "dihaploid" and are essentially not segregating any more (stable).

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the terms "introgression", "introgressed" and "introgressing" refer to the process whereby genes, a QTL or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

"Genetic engineering", "transformation" and "genetic modification" are all used herein as synonyms for the transfer of any kind of genetic information into the DNA of the target plant, usually but not exclusively the chromosomal DNA or genome, of another organism. Genetic engineering is one method of stably integrating heterologous genetic material in the genome of a recipient plant and may include a process comprises transforming cells or tissue of a plants with a DNA recombinant containing a heterologous DNA including a foreign nucleotide sequence encoding a gene or allelic variant thereof as well as the regulatory elements selected among those which are capable of causing the stable integration of heterologous DNA in plant cells or tissue and of enabling the expression of foreign nucleotide sequences in plant cells or plant tissue.

As used herein, the phrase "genetic or molecular marker" refers to a feature of an individual's genome (e.g., a nucleotide or a polynucleotide sequence that is present in an individual's genome) that is associated with one or more lad of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic or molecular marker can be physically located in a position on a chromosome that is within or outside of to the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a very low rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "Restriction Fragment Length Polymorphism" or "RFLP" means a variation between individuals in DNA fragment sizes cut by specific restriction enzymes. Polymorphic sequences that result in RFLPs are used as markers on genetic linkage maps.

"Marker-based selection" is understood within the scope of the invention to refer to e.g. the use of genetic markers to detect one or more nucleic acids from the plant, where the nucleic acid is associated with a desired trait to identify plants that carry genes, QTL or haplotype for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

A "single nucleotide polymorphism" (SNP) is a DNA sequence variation occurring when a single nucleotide, A, C, G, T, in the genome (or other shared sequences as mitochondrial DNA) differs between a set (paired) chromosomes of an individual or differs between members of a species.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Capsicum* used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labeled DNA or RNA sequence which can be used to detect the presence of and to quantify a complementary sequence by molecular hybridization.

As used herein, the term "population" means a genetically homogenous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "pepper" or "*Capsicum*" means any species, variety, cultivar, or population of the *Capsicum* genus.

A "cultivated *Capsicum*" plant is understood within the scope of the invention to refer to a plant that is no longer in the natural state but has been developed by human care and for human use and/or consumption.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

"Backcrossing" is understood within the scope of the invention to refer to a process in which a hybrid progeny is repeatedly crossed back to one of the parents. Different recurrent parents may be used in subsequent backcrosses.

The following description is provided, alongside all chapters of the present invention, so as to enable any person skilled in the art to make use of said invention. Various modifications, however, will remain apparent to those skilled in the art, since the generic principles of the present invention have been defined specifically to provide a male sterile seedless pepper with unique characteristics as set forth below.

In the process of hybrid seed production male sterile inbreeds are usually used as the female parental line in order to increase the efficiency of hybrid production. Sterile pepper plants grow high and very rapidly. At the top of the plant, they set very small, deformed seedless fruits. Spraying hormones on such plants has not succeeded in inducing "normal" fruit setting. But, as in many pepper traits there is a genetic variation to this phenomenon. Male sterile lines differ in the amount and quality of their seedless peppers.

Within the scope of the present invention pepper lines were discovered that were capable of setting qualitative, high yielding seedless fruits, particularly fruits that did not show deformations. Deformation in this context means that a fruit shows an irregular and unusual form e.g., is not uniform, not symmetric, or as irregular or shows no segmentations.

The size of an SLP fruit can be smaller than of a normal, seed-bearing fruit if compared on an otherwise identical genetic background. The seed-bearing sibling can be up to 5-times larger than its SLP relative. However, it is possible by crossing into different genetic backgrounds to compensate against this smaller size and to obtain seedless pepper fruits which have the same or essentially the same size as a commercial size sweet pepper fruit.

In particular, the SLP fruit at maturity may weigh between 2 grams and 10 grams, particularly between 2.5 g and 5 g, or has a size of 1 cm to 4 cm, particularly of 1.5 cm to 3 cm by 0.5 cm to 5 cm, particularly by 2 cm to 4 cm in diameter.

The "seedless" trait is under the control of a genetic determinant and is permanently expressed in the pepper plants according to the present invention independent of artificial treatment with inducing agents such as, for example, plant hormones or plant extracts, which are commonly used in protected pepper cultivation in the greenhouse to artificially induce parthenocarpy in pepper. The expression of the "seedless" trait in the plants according to the invention is also largely independent of other exogenous factors including the pollination or fertilization process, climatic conditions or seasonal variabilities.

As a result, the plants according to the present invention show excellent fruit setting at all seasons that is also under unfavourable growing conditions such as those present in the winter season in the Arava region in Israel (mediteranean climate), where the average medium temperature is in a range of between 4° C. and 14° C., particularly between 6° C. and 12° C.

In one embodiment of the invention, a male sterile seedless pepper (SLP) plant was developed which is characterized by its ability to set seedless fruit throughout the plant. The fruits are small in size such that they can typically be consumed in a single bite.

In particular, the isolated male sterile seedless pepper plant line exhibits characteristic features including those selected from the group consisting of (1) excellent fruit setting at all seasons; (ii) strong & hardy plant; (iii) weak apical dominance as compared with non-sterile peppers resulting in many side branches and ramifications of twigs; (iv) tendency to set two fruits per node in about 20% of nodes; (v) fairly uniform size and shape; (vi) short intervals between nodes, approx. 10 cm long; (vii), fruit production begins from the first nodes and progresses along the length of the branches, similar to non-sterile plants; and, (viii) the flower has small anthers without pollen.

Further, the pepper fruits growing on said isolated plant line exhibits characteristic features including those selected from the group consisting of (i) seedless fruits; (ii) red pigmented in mature and green in premature (unripe) fruits; (iii) conic-like shape, i.e., between bell and classic conic; (iv) size between about 2 to 4 cm long by about 3 to 4 cm in diameter; and (v) very sweet taste (Brix about 8 to about 11°);

The present invention provides experimental evidence that suggests that the "seedless" trait shown by the plants of this invention are genetically controlled. In particular, it appears that the "seedless" trait is multigenic and facultative. When these plants and varieties are pollinated, either by insect or by hand labor, fruit set and development occur normally. However, under conditions in which pollination is difficult or does not occur, these plants and varieties nevertheless set fruit that develops normally, whereas conventional plants and varieties of the prior art might not set fruit at all, or the fruit will set but will often be deformed and/or immediately begin to rot from the blossom end, and fruit development is poor at best, eventually being overtaken by the rot proceeding from the blossom end.

The "seedless" trait can be introgressed in any other plant or plant line of the *Capsicum* genus by a method selected from the group consisting of breeding, single trait conversion and transformation. In particular, the "seedless" trait can be introgressed into commercial pepper lines and varieties by methods known to those skilled in the art of plant breeding.

Commercial peppers are generally hybrids produced from the cross of two parental lines (inbreds). The development of hybrids requires, in general, the development of homozygous inbred lines, the crossing of these lines, and the evaluation of the crosses.

Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and labour and time consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc. A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid performance (hybrid vigor or heterosis), can be manifested in many polygenic traits, including increased vegetative growth and increased yield. Breeding in peppers can be accelerated by the use of double haploids obtained by anther culture. Such a technique gives the possibility to secure the process by producing pure lines in a shorter period of time than the regular pedigree breeding process. Plants within the *Capsicum* genus can be easily cross-pollinated. A trait is also readily transferred from one pepper plant to another plant, including pepper plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait, particularly the "seedless" trait according to the present invention. The progeny of this cross is then mated back to the recurrent parent followed by selection in the resultant progeny for the trait. After three, preferably four, more preferably five or more generations of backcrosses with the recurrent parent with selection for the trait, particularly the "seedless" trait according to the present invention, the progeny is heterozygous for the locus harboring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross. Male sterility is available in pepper. In particular genetic male sterility is widely used in commercial lines. e.g., sweet pepper lines (see for example Daskatoff S. (1972), while in chili pepper also cytoplasmic male sterility (Peterson, 1958) is used. Male sterile pepper mutants and their utilization in heterosis breeding. Eucarpia, meetings on genetic and breeding. Turin 1971, 205-210).

Accordingly, in one embodiment, the present invention relates to a method of producing a seedless pepper plant comprising the steps of
  i) providing seeds of an inbred line of a F1 hybrid of a seedless pepper plant which is male sterile as a female line and a male-fertile (seed-bearing) pepper plant as a male line;
  ii) germinating said seed and growing a mature, fertile plant therefrom;
  iii) inducing self-pollination of said plant grown under (ii), growing fruits and harvesting the fertile seeds therefrom, and
  iv) growing plants from the seeds harvested under and, optionally, selecting plants which grow seedless fruits.

Pepper is a self-pollinated species, so normally a plant can be easily recognized as seedless only if it is also sterile. Theoretically, these 2 phenomena are not interconnected with each other in the sense of being genetically linked, but practically, parthenocarpy can be easily identified when the plant has the 2 traits together. Using fertile plants would require cutting open the fruit to determine whether seeds are present or not.

In one aspect of the invention, plants expressing the "seedless" trait and thus growing seedless pepper fruits, may be identified and selected by simple visual observation of the flowers and identifying male sterile individuals. After distinguishing the sterile plants, they are re-planted and estimated for their seedless fruit setting ability. This can be achieved, for example by examining the plant for the following phenotypic characteristics:
  1. Fruit setting has started in the first nodes, as in fertile plants.
  2. Fruit setting occurs independently from the pollination and/or fertilization process in all the seasons when also fertile plants normally set.
  3. Fruit setting occurs independently from the pollination and/or fertilization process under unfavorable condition.

In the alternative, marker-assisted breeding may be employed to identify those individuals where invention relevant loci and/or flanking marker loci or marker loci genetically linked thereto, have favorable genotypes, particularly homozygous favorable genotypes.

Thus, markers can be developed by methods known to the skilled person and used to identify and select plants according to the present invention and as disclosed herein before with an allele or a set of alleles of locus or loci representing the seedless trait. There are several methods or approaches available, known to those skilled in the art, which can be used to identify and/or develop markers in linkage disequilibrium and/or linked to and/or located in the genome region where the gene(s), QTL or haplotype for the seedless trait resides, as well as markers that represent the actual causal mutations underlying the seedless trait. Without being fully exhaustive some approaches, known by those skilled in the art, include:

candidate gene approach; candidate gene sequences or candidate gene linked sequences can be searched for polymorphism associated and/or genetically linked with the trait of interest and once associated and/or genetically linked those polymorphism can be used in marker assisted breeding applications.

Bulk segregant analysis (BSA) approach (Michelmore at al., 1991); following phenotyping of a population, plants (usually between 5-40) with contrasting phenotypes of the trait of interest are grouped, with the groups forming bulks representing the phenotypic extreme ends of the population. Then the bulks are tested for the presence or absence of molecular marker alleles. Since the bulks are supposed to contrast for alleles contributing to the phenotypic extreme ends, any marker polymorph between the bulks is a candidate genetically linked marker, e.g. linked to the trait of interest and may be used in marker assisted breeding applications, or, alternatively, may be used to genetically map the trait of interest.

QTL mapping or association mapping approach: a population of panel of plants may be characterized for the trait of interest (phenotyped) and genotyped using markers preferably nicely distributed over the entire genome. After obtained genotype data and phenotype data there is searched for patterns of association between the genotype data and phenotype data by joint analysis of genotype and phenotype data using common QTL mapping and/or association mapping software tools. Marker associated with the trait of interest may subsequently be used in marker assisted breeding applications.

Following QTL and/or association mapping, or following genetic mapping of makers linked to the trait of interest, other markers or genes known to be located in the same genomic region (and thus genetically linked) may be identified and used to develop additional markers in the region of interest and/or may be used in marker assisted breeding applications.

Genetically linked markers or marker sequences may also be used to isolate other nucleic acid sequences flanking those markers by hybridization, PCR, and/or 'in-silico' approaches. Those flanking nucleic acid sequences can be used to search for new and/or additional polymorphisms associated and/or genetically linked with the trait of interest which also can be used in marker assisted breeding populations.

Nucleic acid sequences associated and/or genetically linked to the trait of interest may also be used to in comparative genome and/or syntheny mapping approaches to identify homologous region(s) and homologous and/or orthologous sequences and/or candidate genes.

In one embodiment, the present invention therefore relates to a genetic marker that is genetically linked to the genetic determinant controlling the "seedless" trait in a pepper plant according to the invention, particularly in a hybrid pepper plant designated *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X, grown from seeds deposited with NCIMB, Aberdeen AB21 9YA, Scotland, UK on May 26, 2008 under accession number NCIMB 41558, NUMB 41559, NCIMB 41560, NCIMB 41561 and NCIMB 41562, respectively, or a F2 progeny thereof. This genetic marker may be any marker selected from the group consisting of, but not limited to, restriction fragment length polymorphism (RFLP), random amplification of polymorphic DNA (RAPD), amplified restriction fragment length polymorphism (AFLP), single sequence repeats (SSR) and single nucleotide polymorphisms SNPs or any nucleic acid sequence associated and/or genetically linked to the "seedless" trait.

The present invention also relates to a method of developing such a marker including those described herein above, particularly a marker that is genetically linked to the genetic determinant controlling the "seedless" trait in a hybrid pepper plant designated *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X, grown from seeds deposited with NCIMB, Aberdeen AB21 9YA, Scotland, UK on May 26, 2008 under accession number NCIMB 41558, NCIMB 41559, NCIMB 41560, NCIMB 41561 and NCIMB 41562, respectively, or a F2 progeny thereof.

Also embraced by the present invention is the use of such a marker according to the invention for identifying other markers or genes known to be located in the same genomic region (and thus genetically linked) and to develop additional markers in the region of interest and/or in marker assisted breeding applications.

In a further embodiment, the present invention relates to a seedless pepper plant comprising such a marker according to the invention which is genetically linked to the genetic determinant controlling the "seedless" trait in said pepper plant, particularly a marker that is obtainable from a hybrid pepper plant designated *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X, grown from seeds deposited with NCIMB, Aberdeen AB21 9YA, Scotland, UK on May 26, 2008 under accession number NCIMB 41558, NUMB 41559, NCIMB 41560, NCIMB 41561 and NCIMB 41562, respectively, or from a F2 progeny thereof, particularly by applying a method as disclosed herein.

Marker-based selection may already be used in the early phases of inbred development, often in combination with screening methods which are based largely on phenotypic characteristics that can be determined visually and are related to the trait of interest, i.e. the "seedless" trait, and further to key performance indices such as, for example, plant vigor, length of internodes, ramifications, insect resistance, virus resistances such as TMV (Tobacco Mosaic Virus) and TSWV (Tomato Spotted Wilt Virus), etc., which are relevant for the suitability of the plant to be utilized in commercial hybrid production. Selection may also be based on molecular markers, which may or may not be linked to traits of interest.

In particular, marker-based selection may be applied in combination with or followed by a phenotypic selection to identify those individuals where all of the invention relevant loci have heterozygous or homozygous favorable genotypes.

There are several types of molecular markers that may be used in marker-based selection including, but not limited to, restriction fragment length polymorphism (RFLP), random amplification of polymorphic DNA (RAPD), amplified restriction fragment length polymorphism (AFLP), single sequence repeats (SSR) and single nucleotide polymorphisms SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis.

SNPs use PCR extension assays that efficiently pick up point mutations. The procedure requires little DNA per sample. One or a combination of the above methods may be used in a typical marker-based selection breeding program.

Currently, the most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Basically, the method of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerase. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment, that is approximately 2<n>, where n is the number of cycles.

Through PCR amplification millions of copies of the DNA segment flanked by the primers are made. Differences in the number of repeated sequences or insertions or deletions, which are located between the flanking primers in different alleles are reflected in length variations of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

Sequence variations among different alleles which do not result in length variation, like SNPs can be determined (genotyped) by a diverse range of genotyping methods which could be hybridization-based, enzyme-based, or by other post-amplification methods based on physical properties of the DNA, as well as by sequencing.

Alternative methods may be employed to amplify fragments, such as the "Ligase Chain Reaction" ("LCR") (Barely, Proc. Natl. Acad, Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl, Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide," thereby amplifying the di-oligonucleotide, are also known (Wu et al., Genomics 4:560 569 (1989)), and may be readily adapted to the purposes of the present invention.

A molecular marker may thus be DNA fragment amplified by PCR, e.g. a SSR marker or a RAPID marker. The presence or absence of an amplified DNA fragment may be indicative of the presence or absence of the trait itself or of a particular allele of the trait. When using SSR markers, a difference in the length of an amplified DNA fragment may be indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif. Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, a distinction can be made between homozygous plants that carry two copies of the desired, invention-relevant allele at invention-relevant loci and heterozygous plants that carry only one copy and plants that do not contain any copy of the favourable allele(s).

Molecular markers may be used in marker-assisted-selection and/or any other methods wherein plants having or have not the "seedless" trait are traced. The markers may be either trans, or cis markers. A trans marker indicates a polymorphism resulting from introgression of exogenous (donor) DNA into a recipient plant's genome, which polymorphism is linked in cis with the recipient genome, i.e. linked with the opposite allele. Thus, cis markers are linked with the allele of interest, while trans markers are linked with the opposite allele (from the recipient).

To determine the utility of the inbred line and its potential to genetically contribute to the hybrid progeny a test-cross is made with another inbred line, and the resulting progeny phenotypically evaluated. Traits that may be recorded commonly involve traits that are related to fruit shape and fruit characteristics such as pointed or non pointed fruit, pungent or non pungent, red, yellow or orange. Plant characteristics as length of internodes, growing power and ramifications are also considered together with specific virus resistances such as TMV (Tobacco Mosaic virus) and TSWV (Tomato Spotted wilt virus).

For genotyping, or association mapping DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire pepper genome.

Joint-analysis of genotypic and phenotypic data can be performed using standard software.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Isolation of a Seedless Pepper Line 1.1 Growth and Cultivation Conditions: The SLPs of the present invention were grown at Netiv HaHasara and Zofar (Israel) for two growing seasons, i.e., spring and summer 2006; and fall and winter 2006-2007. As in most plants, especially peppers, the described characteristics are related to growth, seasons and conditions. It can be assumed that under other conditions, the plant characteristics may well differ. The following example is presented:

Netiv HaHasara conditions: unheated plastic covered greenhouse, covered by shading net (40%, from May); sandy soil; sowing in February 2006; 2,500 plants per 1,000 m²; Spanish-style side support cane; non-pruning of fruits and plants, as in accepted commercial practice.

Zofar conditions: unheated net house while using double nets, one white netting (25 MESH, 20% shading) throughout season and black netting, 40% shading for the first 40 days, and the last two months of the growing season (i.e., February and March), sandy soil; sowing in July 2006; 3,500 plants per 1,000 m²; Spanish-style side support cane; non-pruning of fruits and plants, as in accepted commercial practice.

1.2 Pedigree Information: The pedigree of one such seedless plant is as shown in the scheme below:

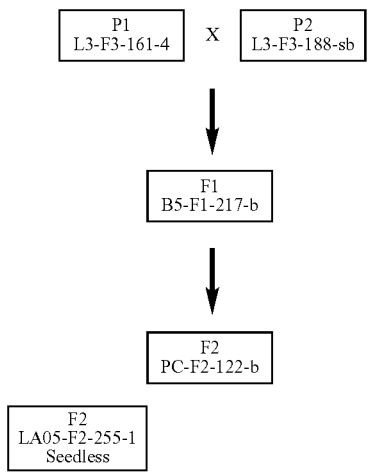

The source of P1 and P2 are F2 seeds of commercial varieties grown in field L3. The population of P2 (the plot L3-188) was divided by sterility. P1 and P2 were selected according to their strong plants and quite good quality. P1 was made from seeds from a fertile plant, No 4, in the plot "L3-161" and P2 is a bulk of seeds from many fertile plants in the plot L3-188. Both were red pepper type. The hybrid "B5-F1-217-b" was made by these 2 plants, where P1 was the male parent and P2 was the female. The hybrid was grown (15 plants) in the field PC in plot 122, and F2 seeds were collected from all the plants. These F2 seeds were sowed in the field L5 in plot 155. This population was split by sterility. Among many other sterile plants plant number 1 was distinguished by its ability to set seedless small fruit all along the plant. The plant was vegetatively multiplied and the offspring were grown in the fall-winter season. In this season the performance of these plants was very similar to spring-summer.

1.3 Plant and Fruit Characteristics: The experiments provided fruits and plants (See pictures 1 and 2), defined by the following: Seedless fruit characterized by (i) seedless; (ii) Red pigmented in mature and dark green pigmented in premature (unripe) fruits; (iii) conic-like shape, i.e., between bell and classic conic; (iv) size is between about 2 to 4 cm long by about 3 to 4 cm in diameter; and (v) very sweet taste (Brix about 8 to about) 11°). The seedless plant is characterized by features selected from a group comprising inter alia of (i) Excellent fruit settings at all seasons; (ii) Strong & hardy plant; (iii) Many side branches, ramifications of twigs, weak apical dominance; (iii) Tendency to set two fruit per node in about 20% of nodes; (iv) Fairly uniform size and shape; (v) Short intervals between nodes, approx. 10 cm long; (vi), fruit production begins from the first nodes and progresses along the length of the branches, similar to non-sterile plants; and, (vii) the flower has small anthers without pollen.

Example 2

Genetics of the "Seedless" Trait

To demonstrate that the "seedless" trait, discovered in the "one-bite" pepper type, is an independent trait controlled by a genetic determinant and can therefore be passed on genetically to many different pepper types, it is shown that the trait will be present in offspring of populations made by crossing the seedless plant with other pepper type plants.

2.1 Breeding History: In spring 2007, the SLP variety 255-1 was crossed with 8 varieties of different types; Blocky, Kapya and Conic. The hybrids were grown in autumn/winter 2007-2008 and F2 seeds were harvested from 10 F1 plants.

| The Hybrid Name | Description | Male Name | Female Name |
|---|---|---|---|
| 1 AR07-F1-56-b | Hybrid 255-1 x Kapya | NJ06-F3-385-4 (Kapya) | AR06-F3-255-1 |
| 2 AR07-F1-87-b | Hybrid 255-1 x Kapya | NA06-F3-14-4 (Kapya) | AR06-F3-255-1 |
| 3 AR07-F1-166-b | Hybrid 255-1 x Conic | NJ06-F3-378-1 (conic) | AR06-F3-255-1 |
| 4 AR07-F1-171-x | Hybrid 255-1 x Blocky | AV05-F1-7158-TT (Blocky) | AR06-F3-255-1 |
| 5 AR07-F1-172-x | Hybrid 255-1 x Blocky | AV05-F1-7181-TT (Blocky) | AR06-F3-255-1 |

Example 3

Recovery of the "Seedless" Trait from the Hybrids 3.1 Experimental Design: The 5 deposited hybrids were grown from samples of the deposited seed, 10 individual plants for each (50 plants in total). F2 seeds from the individual plants were obtained by self pollination. The F2 seeds were harvested from the plants and kept separate. 55 F2 seeds from each F1 plant were sown (2,750 seeds in total, 550 seeds per hybrid family). The target was to achieve 100-130 sterile F2 plants from each deposited hybrid family (~25% of 550). The trial was designed so that each F2 offspring was separately transplanted. Additionally, as a control, F2 seeds from the original hybrid, where the SLP trait was discovered in the offspring, were also sown: 600 seeds from 3 F1 plants, 200 seeds from each. The F2 Plants are than analyzed for expression of a male sterile (MS) trait and the seedless pepper (SLP) trait. Both traits segregate separately, however the MS trait is necessary to have the SLP trait phenotypically expressed. While in the female line (SLP line) the MS trait is homogenous recessive, in the F1 hybrid it is heterogenic (the male lines are all homogenous male fertile).

As a backup, additional seeds were sown a week later. This sowing cycle included the families sown in the first cycle (in case the germination is insufficient) and F2 families from other hybrids to enrich the potential variation.

About 1 to 2 month later, the seedlings are transplanted to pots and continue to grow in the nursery. The screening and selection of seedless sterile plants is done by simple observation of the flowers. After distinguishing the sterile plants, they are planted in net house (white net 50 mash to avoid cross pollination by insects) at a density of 2,500 plants/1,000 m$^2$. Parthenocarpic phenotyping is done 2 weeks later.

3.2 Results: The male sterile trait (MS), which is comprised in the F2 seeds, is expressed with an average rate of 27% (not far from the theoretical rate 25% which is expected for a monogenic recessive trait). The SLP trait can only be phenotypically expressed in a MS background. The average rate of plants expressing the SLP trait in a population of MS plants is 23%. Although the SLP trait is not dependent on environmental conditions, the degree of expression can be influenced by the genetic background of the male line. It ranges from 6% (original hybrid) up to 36% in the hybrid AR07-F1-56-b made by crossing the SLP plant (AR06-F3-255-1) with Kapya line. In all trials based on the deposited lines the SLP trait could be consistently recovered. The data indicate that the SLP trait is a complex trait with at least 2 primary genetic components involved.

In all SLP plants, 100% of the fruits were seedless, and of all these fruits were 100% seedless (no ovules were fertilized to become seed bearing). In negative fertile control only very occasionally some individual fruits on a plant were discovered to be seedless; however this is the result of climate effects or irregular pollination but not a genetic phenomenon.

Deposits

The following seed samples of *Capsicum annuum* lines were deposited with NCIMB, Aberdeen AB21 9YA, Scotland, UK on May 26, 2008 under the provisions of the Budapest Treaty:

| *Capsicum annuum* seed line designation | Deposition date | Accession No |
|---|---|---|
| AR07-F1-56-b | 26 May 2008 | NCIMB 41558 |
| AR07-F1-87-b | 26 May 2008 | NCIMB 41559 |
| AR07-F1-166-b | 26 May 2008 | NCIMB 41560 |
| AR07-F1-171-X | 26 May 2008 | NCIMB 41561 |
| AR07-F1-172-X | 26 May 2008 | NCIMB 41562 |

List of References

Sjut V, Bangerth F (1982) "Induced parthenocarpy: a way of changing the levels of endogenous hormones in tomato fruits (*Lycopersicon esculent* Mill.): 1. Extractable hormones." Plant Growth Regul 1: 243-251

Kim I S, Okubo H, Fujieda K. 1992. "Endogenous levels of IAA in relation to parthenocarpy in cucumber (*Cucumis sativus* L.)." Scientia Horticulturae 52: 1-8.

Beyer E M, Quebedeaux B. 1974. "Parthenocarpy in cucumber: mechanism of action of auxin transport inhibitors." Journal of the American Society for Horticultural Science 99: 385-390.

Heuvelink and Körner "Parthenocarpic Fruit Growth Reduces Yield Fluctuation and Blossom-end Rot in Sweet Pepper", Annals of Botany. 88(1):69-74, (2001)

Rieger, R. et al, A "Glossary of Genetics and Cytogenetics, Classical and Molecular Book Microbes Human", George Allen & Unwin Ltd.; Springer-Verlag, London; Berlin, UK; Germany; 1968. 3rd ed. (rev.), 507 pp International Convention for the Protection of New Varieties of Plants (UPOV treaty), of Dec. 2, 1961, as Revised at Geneva on Nov. 10, 1972, on Oct. 23, 1978, and on Mar. 19, 1991

Poehlman & Sleper (1995) "Breeding Field Crops", 4th Ed., 172-175; Fehr (1987) Principles of Cultivar Development, Vol. 1: Theory and Technique, 360-376, Daskaloff S. 1972. Male sterile pepper (*C. annuum* L.) mutants and their utilization in heterosis breeding. Eucarpia, Meeting on Genetics and Breeding of *Capsicum*. (Torino, Italy), pp. 205-210.

Peterson, 1958 "Cytoplasmically inherited male-sterility in *Capsicum*." Am. Nat. 92:111-119.

Michelmore, R. W., Para, I., and Kasseri, R. V. (1991). "Identification of markers linked to disease-resistance genes by bulked segregant analysis: a rapid method to detect markers in specific genomic regions by using segregating populations." Proc. Natl. Acad. Sci., USA, 88: 9828-9832

Mullis et al., "Specific enzymatic amplification of DNA invitro the polymerase chain reaction." Cold Spring Harbor Symp. Quant. Biol. 51:263-274 (1986)

Barany, "Genetic disease detection and DNA amplification using cloned thermostable ligase" Proc. Natl. Acad. Sci. (U.S.A.) 88:189 193 (1991)

Landegren et al., "A ligase-mediated gene detection technique" Science 241:1077 1080 (1988)

Nickerson et al., "Automated DNA diagnostics using an ELISA-based oligonucleotide ligation assay" Proc. Natl. Acad. Sci. (U.S.A.) 878923-8927 (1990)

Wu et al., "The ligation amplification reaction (LAR)—amplification of specific DNA sequences using sequential rounds of template-dependent ligation." Genomics 4:560-569 (1989)

PCT Application WO 90/01069

The invention claimed is:

1. Seed for growing a hybrid pepper plant selected from the group consisting of a hybrid pepper deposited under NCIMB 41558, NCIMB 41559, NCIMB 41560, NCIMB 41561 and NCIMB 41562.

2. A pepper plant, which is selected from the group consisting of a hybrid pepper designated *Capsicum annuum* AR07-F1-56-b; *Capsicum annuum* AR07-F1-87-b; *Capsicum annuum* AR07-F1-166-b; *Capsicum annuum* AR07-F1-171-X; and *Capsicum annuum* AR07-F1-172-X, grown from seeds deposited with NCIMB, Aberdeen AB21 9YA, Scotland, UK on May 26, 2008 under accession number NCIMB 41558, NCIMB 41559, NCIMB 41560, NCIMB 41561 and NCIMB 41562, respectively.

3. A pepper plant according to claim 2, wherein fruit setting starts at the first nodes of a branch and progresses along the length of the entire branch.

4. A pepper plant according to claim 3, wherein said plant grows two fruits per node in about 20% of the nodes.

5. The plant according to claim 2, wherein said plant grows a sweet pepper selected from the group consisting of a conical pepper, a long conical pepper and a blocky-type pepper.

6. The plant according to claim 2, which grows pepper fruits which are red pigmented in the mature and dark green pigmented in the premature or unripe stage.

7. Plant material obtained from a plant according to claim 2.

8. Plant parts of a plant according to claim 2.

9. A fruit of a plant according to claim 2.

10. A fruit according to claim 9 which is a processed fruit.

* * * * *